United States Patent [19]

Omura

[11] Patent Number: 5,188,107
[45] Date of Patent: Feb. 23, 1993

[54] BI-DIGITAL O-RING TEST FOR IMAGING AND DIAGNOSIS OF INTERNAL ORGANS OF A PATIENT

[76] Inventor: Yoshiaki Omura, 800 Riverside Dr., Apt. 8-L, New York, N.Y. 10032

[21] Appl. No.: 479,195

[22] Filed: Feb. 13, 1990

Related U.S. Application Data

[63] Continuation of Ser. No. 113,394, Oct. 22, 1987, abandoned, which is a continuation of Ser. No. 785,495, Oct. 8, 1985, abandoned.

[51] Int. Cl.$^5$ ............................................. A61B 5/00
[52] U.S. Cl. .................................................... 128/630
[58] Field of Search ........................ 128/630, 653, 665

[56] References Cited

U.S. PATENT DOCUMENTS

| | | | |
|---|---|---|---|
| 4,467,812 | 8/1984 | Stoller .................................. | 128/665 |
| 4,552,151 | 11/1985 | Bolomen et al. ..................... | 128/653 |
| 4,554,925 | 11/1985 | Young .................................. | 128/653 |
| 4,572,198 | 2/1986 | Codrington .......................... | 128/653 |
| 4,583,867 | 4/1986 | Chive et al. ......................... | 128/653 |

Primary Examiner—Francis Jaworski
Attorney, Agent, or Firm—Kane, Dalsimer, Sullivan, Kurucz, Levy, Eisele & Richard

[57] ABSTRACT

A method of imaging an internal organ of a patient for purposes of medical diagnosis, where a patient forms an O-ring shape with one of hands by placing the fingertips of his thumb and one of his remaining fingers together and a sample of tissue of an internal organ is placed on the patient's other hand, and the patient's internal organ is non-invasively externally probed with a probing instrument. The internal organ is the same type of organ as that of the sample. Simultaneously a tester attempts to pull apart the O-ring shape by means of the tester placing his thumb and one of the remaining fingers of each of his hands within the O-ring shape of the patient to form interlocking O-rings and pulling the thumb and the finger of the patient apart due to an electromagnetic field of the tissue of the sample interacting with an electromagnetic field of the internal organ being probed and this interaction is detected by the ability to pull apart the O-ring shape thereby permitting imaging of the boundaries of the internal organ being probed.

15 Claims, 11 Drawing Sheets

FIG. 13

BI-DIGITAL O-RING TEST FOR IMAGING AND DIAGNOSIS OF INTERNAL ORGANS OF A PATIENT

This is a continuation of co-pending application Ser. No. 113,394, filed on Oct. 22, 1987, and now abandoned, which is a continuation of Ser. No. 785,495, filed Oct. 8, 1985, and now abandoned.

BACKGROUND OF THE INVENTION

The present invention relates to a method for imaging the various organs of the body when employing a bi-digital O-ring technique.

Previously there have been many methods of imaging internal organs with various advantages and limitations. However, one common negative aspect of these previously known methods is that they all expose the body to radiation such as from X-rays, gamma rays, ultrasonic, strong magnetic fields or other potentially dangerous conditions. It therefore would be advantageous to provide a new simple method of imaging internal organs which has a significant diagnostic thereapeutic implication while avoiding the hazards of the prior art and which is simple, inexpensive, relatively expeditious method of diagnosis.

SUMMARY OF THE INVENTION

Hence with the foregoing in mind, it is the primary object of the present invention to provide a method which permits imaging of internal organs, localizing exact organ representations at the front and back of the body of a patient and to provide significant diagnostic capabilities.

This object is realized by the present invention which relates to a method of imaging an internal organ of a patient for purposes of medical diagnosis which comprises having the patient place the finger tips of his thumb and any one of his other fingers of one of his hands together to form an O-ring shape.

Determination of which of the other finger is utilized is made by pre-testing for compatability of strength between the patient and the person conducting the test e.g., the tester. For example, the patient will initially form the O-ring shape with his thumb and index finger. The tester will then interlock an O-ring shape comprising his thumb and index finger about the patient's O-ring shape. If the tester and patient are of compatible finger strength then this particular interlocking arrangment of O-ring shape can be used. If the patient and the tester are of compatible strength than the tester should not be able to open the O-ring shape of the patient. If the patient's O-ring opens too easily then the tester should use a weaker finger than his index finger and repeat this pre-testing. If the tester cannot open the O-ring with two or more finger and his thumb, then the patient should use weaker finger in the O-ring shape. After pre-testing and formation the O-ring shape by the patient, sample tissue of an internal organ corresponding to the organ to be imaged is placed on or in the close vicinity of the patient's other hand by means of a microscopic slide or any conventional means. The method further includes non-invasive external probing of an internal organ of a patient with a probing device including a rod-shaped instrument while simultaneously attempting to pull apart the O-ring shape by means of placing the tester's thumb and corresponding remaining finger about the O-ring of the patient and exerting pressure outwardly so that an electromagnetic field of the tissue sample interacts with an-electromagnetic field of any cancerous tissue of the internal organ of the patient being probed and this interaction is detected by the ability to pull apart the O-ring shape.

Further objects and advantages of the invention will set forth in part in the following Specification and in part will be obvious therefrom without being specifically referred to, the same being realized and obtained as pointed out in the claims thereof.

BRIEF DESCRIPTION OF THE DRAWINGS

For fuller understanding of the nature and objects of the invention reference should be made to the following detailed description, taken in connection with the accompanying drawings, in which.

DETAILED DESCRIPTION OF THE PREFERRED EMBODIMENT

Referring now to the drawings, there is shown the methodology of the present invention wherein a bi-digital O-ring technique is being utilized.

Figure 1:
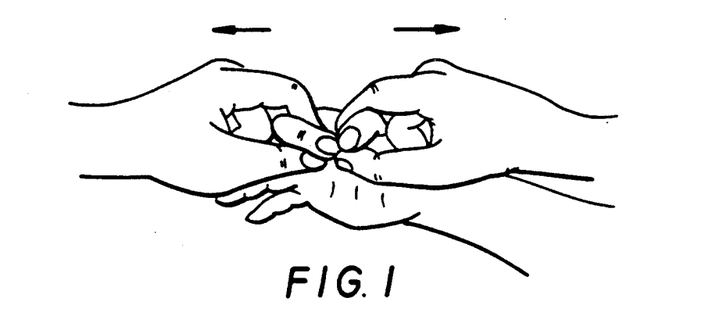
FIGS. 1-4 show the bi-digital O-ring method of the present invention.
Figure 2:
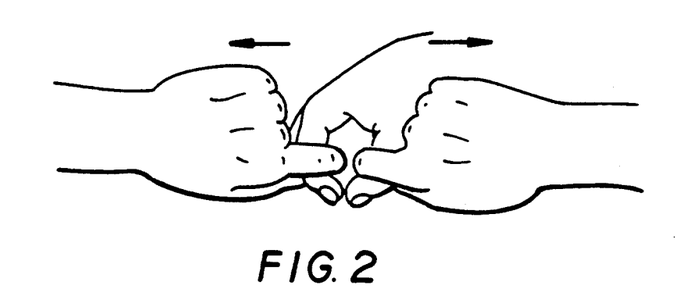
Figure 3:
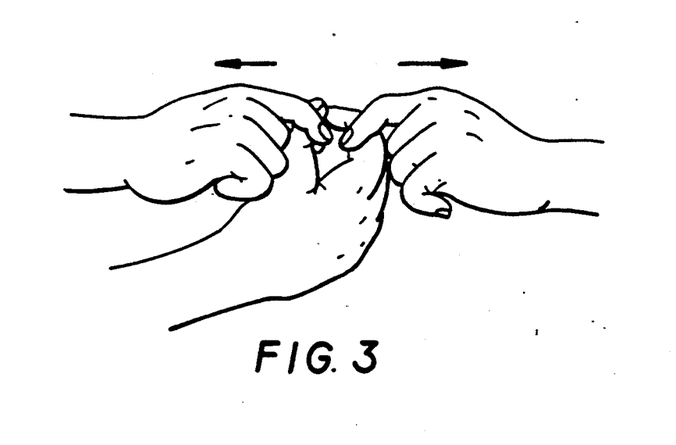
Figure 4:
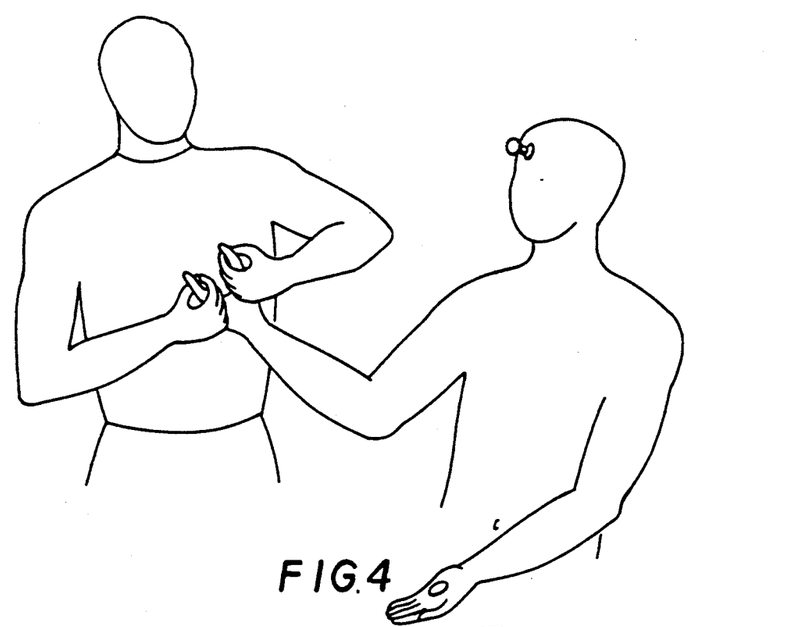
Figure 5:
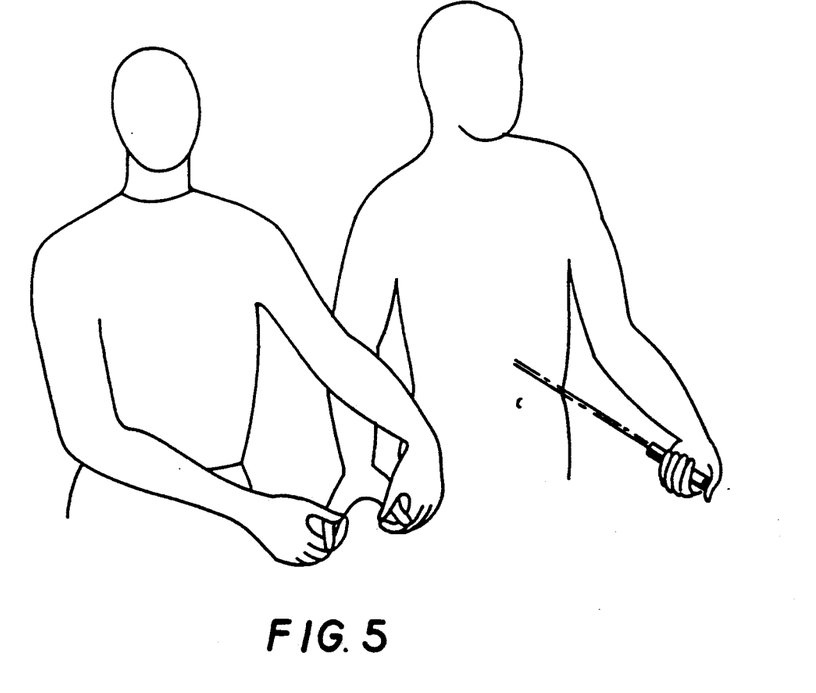
FIG. 5 shows use of a light source as the probing means.
Figure 6:
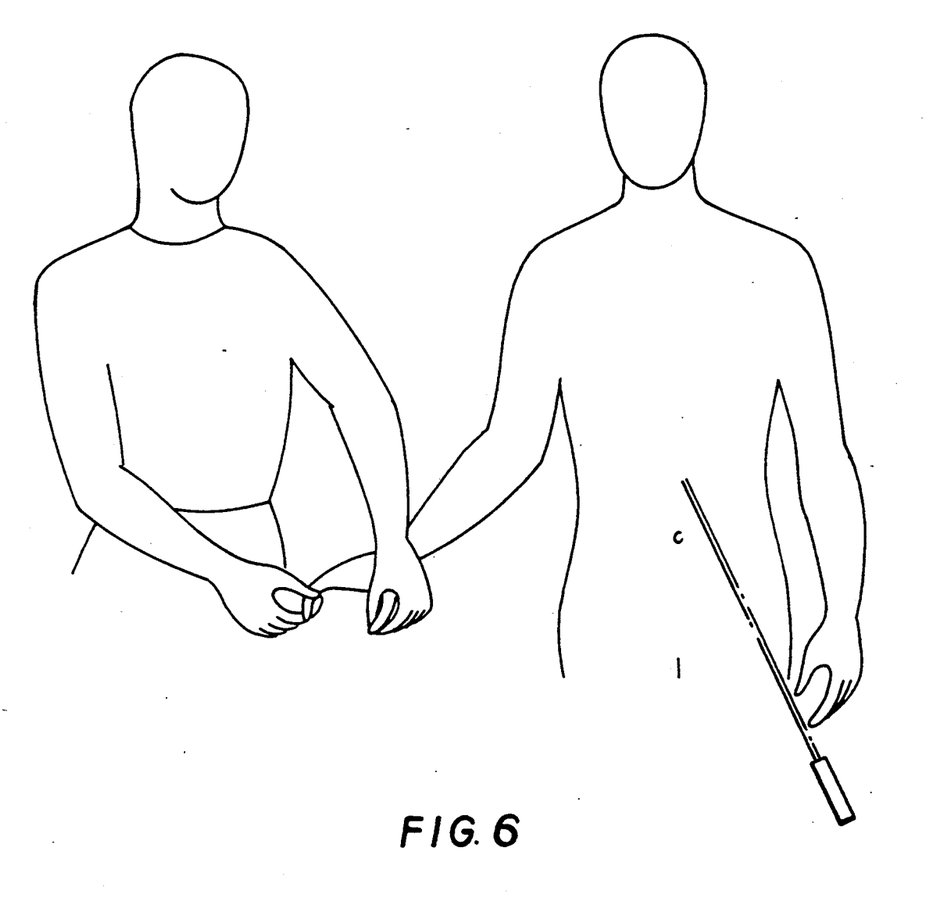
FIG. 6 shows a helium neon laser beam as the probing means at a distance of over 60 cm from the patient.
Figure 7:
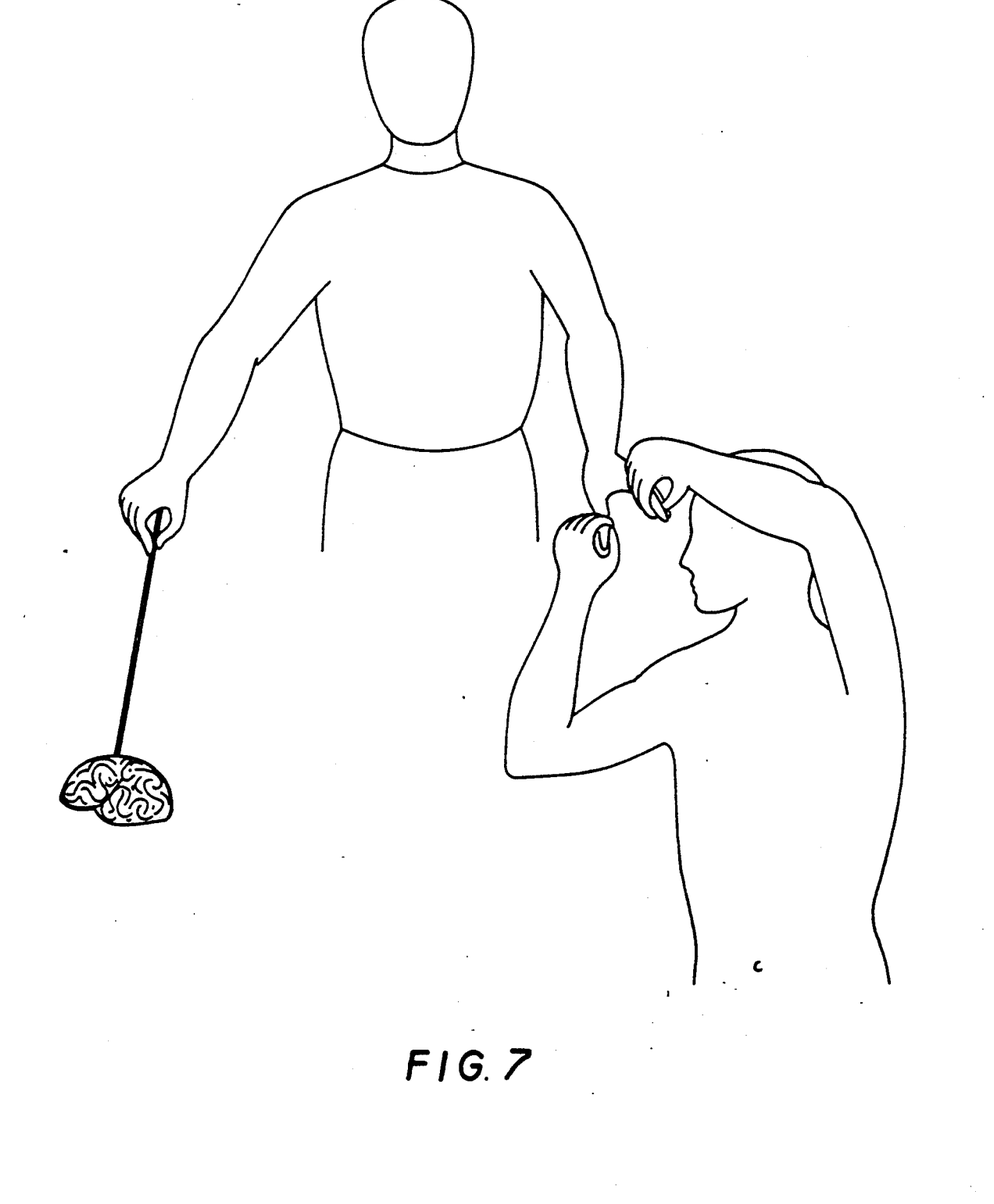
FIG. 7 shows a modification of the method using a third person and a conductor where the test subject is a cat.
Figure 8A:
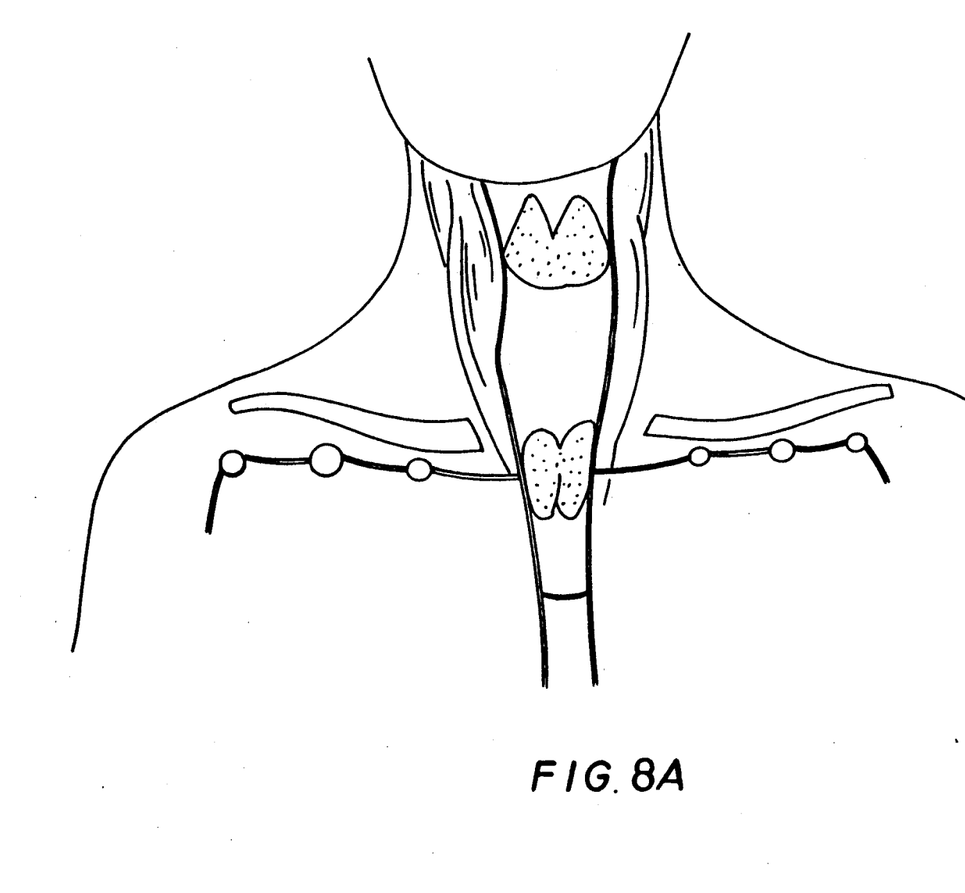
FIG. 8A shows imaging of the right and left thyroid glands and thymus gland network in accordance with the teachings of the present invention.
Figure 8B:
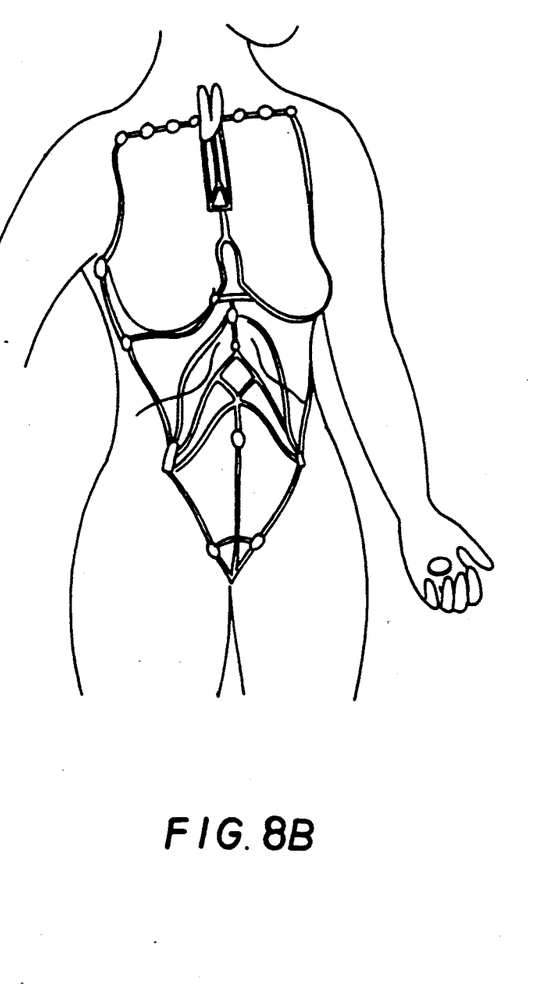
FIG. 8B shows imaging of the thymus gland network where the patient is holding 1 gm of dried thymus gland in accordance with the teachings of the present invention.
Figure 9:
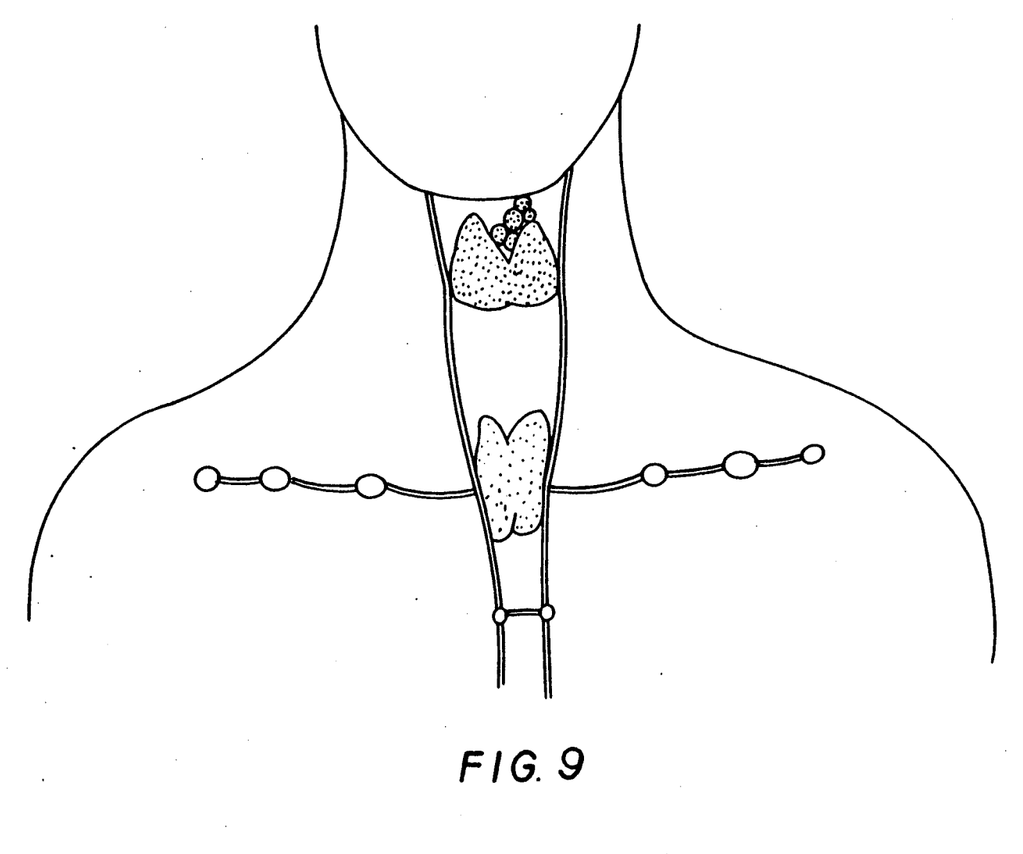
FIG. 9 shows imaging of the right and left thyroid gland (red color) and thymus gland network (white color) in accordance with the teachings of the present invention.
Figure 10A:
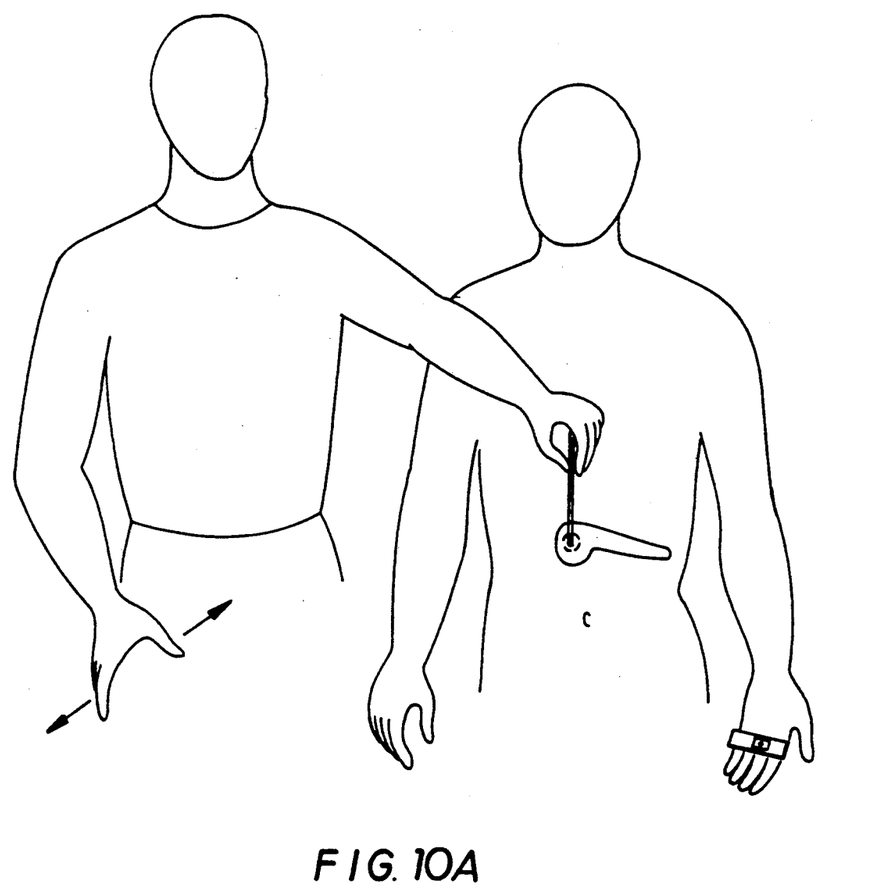
FIG. 10A shows a patient holding a glass slide of pure adeno carcinoma of the head of the pancreas. Note the outline of the pancreas and location of cancer indicated by the tip of the metal wire touching the area.
Figure 10B:
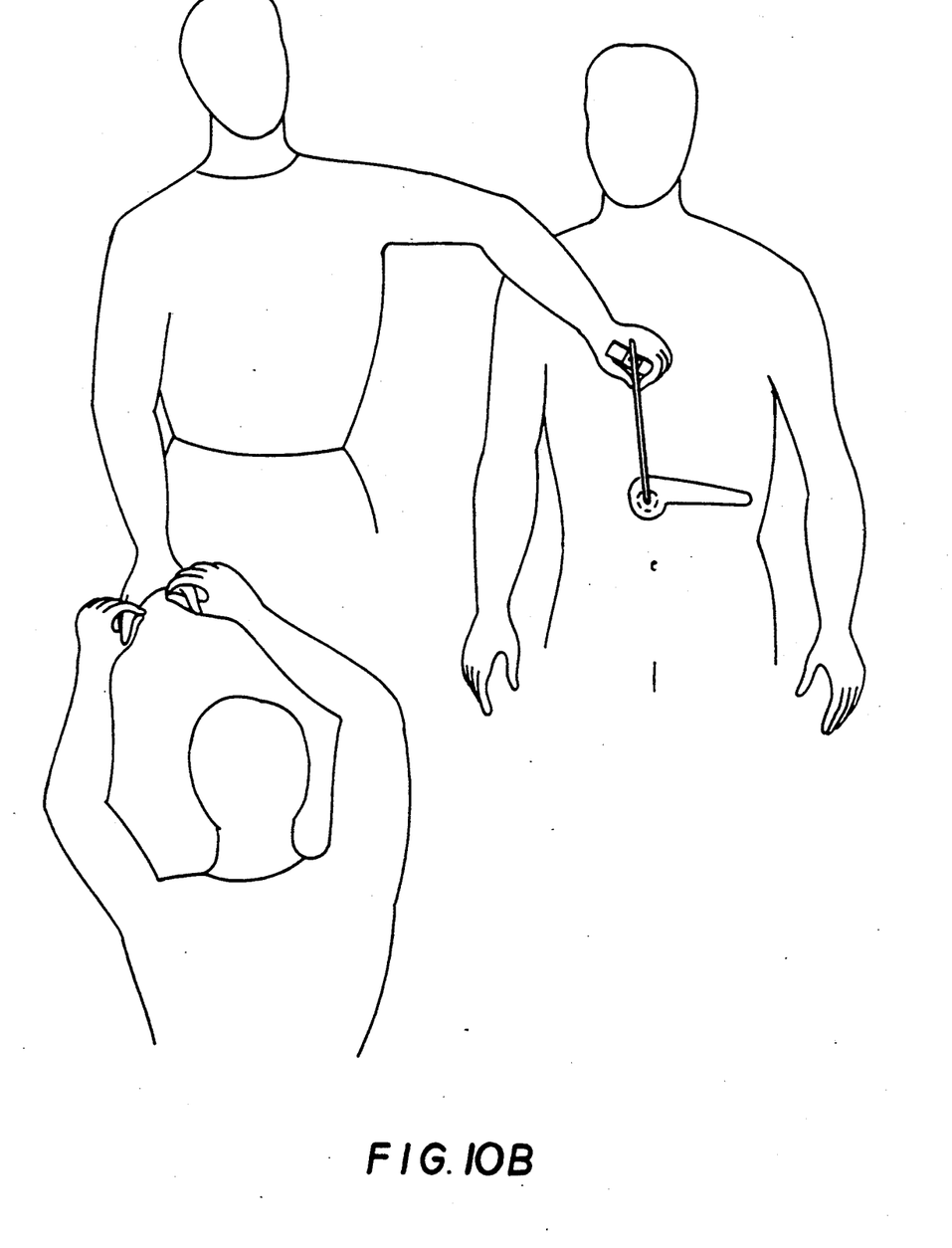
FIG. 10B shows a further modification of the method of the present invention where the patient's finger strength is too weak to be examined and a third person is used for evaluation purposes who is electrically connected to the patient.
Figure 11:
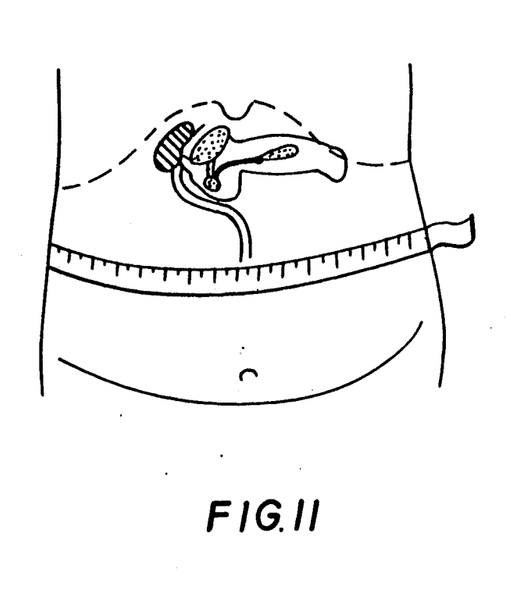
FIG. 11 shows imaging of the pancreas, it's cancer tissue, gall bladder, duodenum and bile duct in accordance with the teachings of the present invention.
Figure 12:
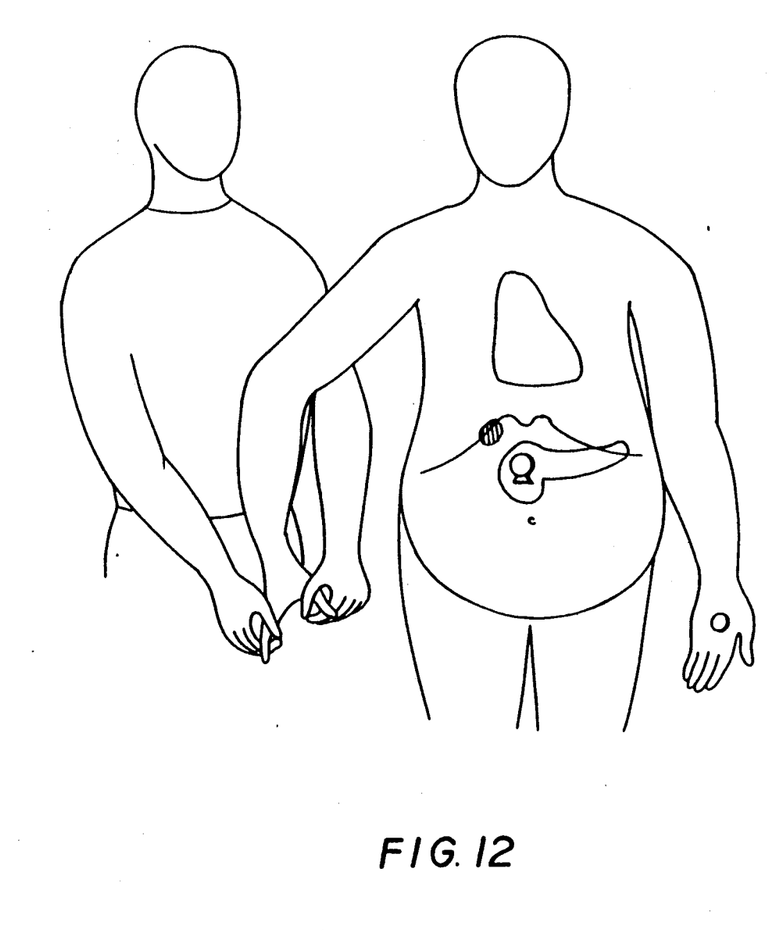
FIG. 12 shows testing for drug compatibility with pancreas imaging from the head of the pancreas in accordance with the teachings of the present invention.
Figure 13:
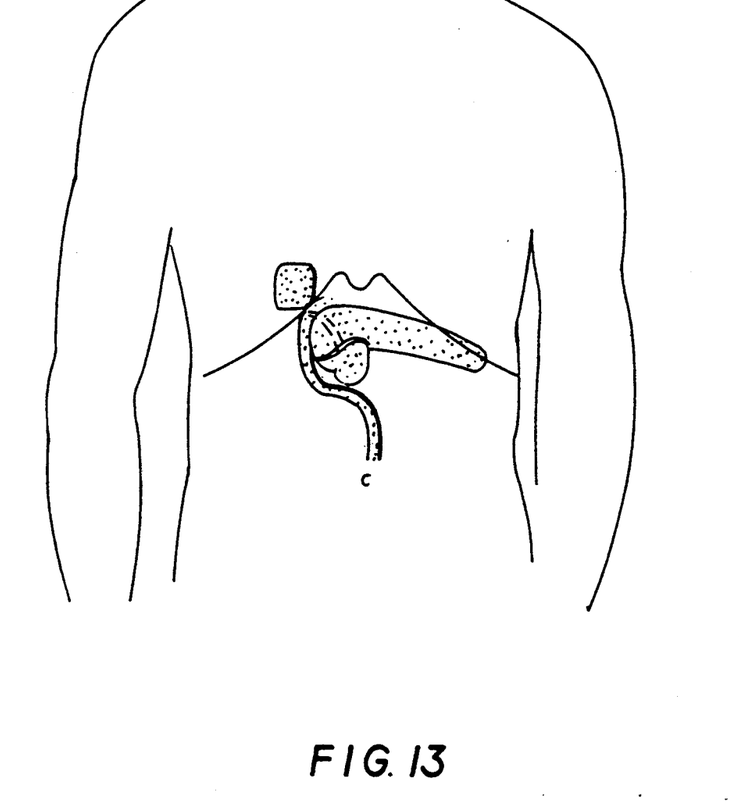
FIG. 13 shows imaging of the entire pancreas with the enlarged head of the pancreas, duodemum, gall bladder, bile duct and pancreatic duct in accordance with the teaching of the present invention.

The fingertips of a thumb and an index finger of one hand of a patient are placed together to form an O-ring shape. In the patient's other hand, a sample containing a pure tissue of an internal organ is deposited (see FIG. 10B). The slide contains the tissue of an internal organ of the same type as that of the probing internal organ of the patient which is to be imaged. Non-invasive external probing means can then be placed near the body surface area above the internal organ of the patent and the bi-digital O-ring test can be employed. The person conducting the test places his thumb and one of his other fingers of each of his hands within the patient's O-ring shape thus forming interlocking O-rings as shown in FIGS. 1–3. The electromagnetic field produced by the tissue will interact with the electromagnetic field of organ being imaged and this interaction would be detected by the ability to pull the thumb and index fingers of the patient apart thereby opening the O-ring shape.

The probing element can be of a mechanical or of a light beam means. One possibility is to use a rod-shaped non-metallic probing instrument having a round shaped tip of a diameter of not greater than 1 mm for the direct examination of the patient.

A different embodiment would involve using a light source or light beam with a wave length longer than a green color i.e. 434 millimicrons. Thus light sources such as yellow, red or infrared would be usable. It would also be possible to use a laser beam or any white light. A light beam must have a small diameter of 1 mm or less for accuracy.

A further embodiment would be the application of a voltage such as the DC battery preferably but not limited to 1.5 volts with the positive terminal of the battery pointed toward the person to be probed.

It is also possible to employ a DC battery in a syringe casing made of insulating material and to aim that in the direction of the internal organ to be imaged. The end of the syringe casing closest to the organ need not be in contact with the organ and has an orifice which should be of a small diameter to permit focusing of the electric field emanating from the DC battery.

It is also possible to use a diode as the probing means which is pointed in a forward biasing direction from the tester toward the patient being probed. This has been tested by the inventor and a electrical current has been noted going through the diode to suggest that an electrical phenomena is occurring. When the diode was reversed in direction, no abnormality was detected by employing this method with a third person.

A further application of the bi-digital O-ring test is that it can also be used to detect a particular type of malignant tumor including cancer within an internal organ of the patient. The method involves placing a sample of a pure cancerous or any other malignant tissue on the patient's hand and testing the organ to be diagnosed by any of the probing means mentioned above and performing the bi-digital O-ring test in the above-described manner. If the patient has a particular type of cancer that is the same type as that of the sample tissue in his hand, then the O-ring technique will cause his thumb and finger to be parted and accordingly the cancerous area can be imaged. By having a set (kit) of all the commonly occurring major malignant tissue samples of different internal organs and testing the response of each of these malignant tissue samples as a form of microscopic slide type of one can routinely and quickly examine whether the patient has one or more type of malignant tumors of any internal organ.

Similarly toxicities or allergies can be tested for by depositing substances to which the patient may exhibit reaction to such as drugs, foods and drinks including aspirin, penicillin, milk products and certain vegetables. A sample of the substance is deposited in the patient's hand, the internal organ to be tested is probed and the bi-digital O-ring test is again performed.

It is also possible to test for particular types of bacteria in a similar manner by depositing the particular type of pure bacteria, preferably by means of a glass slide, in the patient's hand and conducting the bi-digital O-ring test.

Further it is possible to test for the effect of drugs on a patient's existing conditions. A sample of the drug can be deposited in the patient's hand and the internal organ in question can be stimulated to see whether the drug has a good or bad effect on the patient. For example aspirin is known to produce microhemorrhage on the mucus membranes of the stomach and such a toxic effect can be tested for by probing the stomach area with probing means. It is important to note that this method can be employed to determine the optimal or toxic dosage of the drug sample necessary to effect the patent either beneficially or adversely.

In performing the bi-digital O-ring test some patients are stronger or weaker than the tester and therefore rather than use the index finger with the thumb, one of the other fingers of the patient or the tester can be used in order to properly test a patient's condition.

Similarly certain patients are too weak to be tested such as cancer patients and it becomes difficult to test their conditions as the O-ring shape will open easily and it will be difficult to detect a particular type of cancer or bacteria depending on what is being tested for in that patient. It is therefore a further feature of the method of the present invention that a third person be used who is first pretested with the bi-digitial O-ring test. The third person is connected by electrically conductive material to the patient by means of a conductor being placed between the body surface above the internal organ of the patient to be tested and the third person. The bi-digital O-ring is then tested and performed on the third person. This is extremely effective not only for weakened adult patients but also for children or infants as well as for animals where it is not practical to directly apply the methodology of the present invention due to extreme weakness or inability to communicate with these test subjects.

An approximate scale has been worked out for testing the degree of weakness in the patient by means of the bi-digital O-ring test. If the O-ring shape formed by the patient's thumb and finger is opened to the maximum possible width during the bi-digital O-ring test then a number of minus 4 is assigned to it indicating extreme weakness. If the patient's thumb and finger form the O-ring opens to half that distance, then the number of minus 2 is assigned to it. If a patient's thumb and fingers are parted three quarters of the maximum distance then the number of minus 3 is assigned to it. If the patient's thumb and finger open to one quarter of the maximum distance then a number of minus 1 is assigned to it.

If it is necessary for a tester to use two fingers and a thumb in order to test the O-ring shape of the patient and the O-ring does not open than a number of plus 2 is assigned. If it opens, a number somewhere between 0 and plus 2 is assigned. If the tester is forced to use three fingers and the thumb and the O-ring shape does not open than it is assigned a number of plus 3. If it does open then it is assigned a number between plus 2 and plus 3. If the tester uses four fingers and a thumb and it does not open it is assigned a number of plus 4. If it does open, it is assigned a number between plus 3 and plus 4.

Generally speaking a reading of minus 3 and minus 4 indicates that a mass of cancer cells exists in the particular area of the internal organ which is being externally probed of that particular type of cancer. Minus 4 is of course the weakest reading indicating the weakest condition of the patient and plus 4 indicates the strongest condition of the patient and the numbers in between suggests the degrees between these two extremes.

In testing for allergies it is particularly useful to deposit a sample of thymus gland tissue in the patient's hand along with the sample of the substance for which the allergy is being checked for. This is particularly useful for people who have certain allergies to certain drugs like penicillin. For instance amoxicillin is a derivitive of penicillin and can give false compatability yet depositing a sample of amoxicillin along with a sample of thymus gland in the patient's hand and by performing the bi-digital O-ring test these allergies can be determined by weakening the patients finger strength.

Further confirmation of the patient's reaction can be achieved by repeating this procedure and probing his thymus gland.

If the amoxicillin is tested by use of the bi-digitial O-ring test without the thymus gland sample the tester may get a false reading of no reaction to the amoxicillin. It is therefore necessary to test for the reaction to the amoxicillin or to any drug by depositing the drug sample along with the thymus gland sample on the patient's hand when conducting the bi-digitial O-ring test.

I do not limit myself to any particular details of constructions set forth in the Specification and illustrated in the accompanying drawings, as the same referred to and set forth only one embodiment of the invention and it is observed that the same may be modified in the scope of dependent claims without departing from the spirit of the scope of the invention.

Having thus described the invention, what I claim as new and desire to be secured by Letters Patent is as follows:

1. A method of imaging an internal organ of a patient for purposes of medical diagnosis, comprising the steps of:
    having the patient form an O-Ring shape with one of his hands by placing the fingertips of his thumb and one of his remaining fingers together;
    placing a sample of tissue of an internal organ on or about the close vicinity of the patient's other hand; and
    non-invasive external probing of the patient with probing means, the internal organ being the same type of organ as that of the sample and simultaneously attempting to pull apart the O-Ring shape by means of a tester placing his thumb and one of his remaining fingers of each of his hands within the O-Ring shape of the patient to form interlocking O-Rings to form interlocking O-Rings and pulling the thumb and the finger of the patient apart whereby an electromagnetic field of the tissue of the sample interacts with an electromagnetic field of the internal organ being probed and this interaction is detected by the ability to pull apart the O-Ring shape by the tester's O-Rings of compatible strength thereby permitting imaging of the boundaries of the internal organ being probed.

2. A method according to claim wherein said probing means is a rod-shaped non-metallic instrument having a round-shaped tip with a diameter no greater than 1 mm.

3. A method according to claim 1 wherein said probing means is a light beam having a wavelength greater than a green color and said light beam having a small diameter not greater than 1 mm.

4. A method according to claim 1 wherein said probing means includes an application of a voltage such as a D.C. battery of preferably 1.5 volts and the positive terminal of said battery is pointed toward but not necessarily touching the internal organ to be probed.

5. A method according to claim 4 wherein said voltage is focused by means of a syringe casing made of insulating material in which said DC battery is housed therein and the positive terminal of the battery is facing toward the narrow orifice of the casing, said narrow orifice having a sufficiently small diameter to focus the electromagnetic field of said battery.

6. A method according to claim 1 wherein said organ sample is a human organ.

7. A method according to claim 1 wherein said organ sample is any mammal organ such as that of a cow, monkey or pig.

8. A method according to claim 1 wherein a metallic conductor is connected between a third person and the patient and one end of said conductor is placed against the organ to be probed of the patient and the bi-digital O-ring test is performed on the third person.

9. A method according to claim 1 wherein instead of a sample of organ tissue, a substance is placed in the patient's hand and the patient's internal organ is probed for any toxic or allergic reactions to the sample substance.

10. A method according to claim 8 wherein said substance includes a drug, food or drink.

11. A method according to claim 1 wherein instead of a sample of organ tissue, a drug sample is placed in the patient's hand and the patient's internal organ is probed for any positive or negative reaction to the drug sample.

12. A method according to claim 1 wherein said probing means include a small suction cup.

13. A method according to claim 1 wherein the compatible strength of the tester's O-Rings is determined by pretesting for compatibility of strength between the patient and the tester, the patient initially forming the O-Ring shape with this thumb and index finger and the tester interlocking his O-Ring shape with his thumb and index finger so that if the patient is weaker than the tester the patient's O-Ring opens too easily and the tester uses a weaker finger than his index finger and repeats the pretesting, if the tester is unable to open the patient's O-Ring with two or more fingers and his thumb than the patient uses a weaker finger and pretesting is repeated.

14. A method of imaging an internal organ of a patient for purposes of medical diagnosis, comprising the steps of:
    having the patient form an O-ring shape with one of his hands by placing the thumb and one of his remaining fingers of one of hands together;
    placing a sample of a particular type of malignant tissue including cancerous tissue of an internal organ on or about the close vicinity of the patient's other hand; and
    non-invasive external probing of an internal organ of the patient with probing means, the internal organ being the same type of organ as that of the sample and simultaneously attempting to pull apart the O-ring shape by means of a tester placing his thumb and one of the remaining fingers of each of his hands within the O-ring shape of the patient's to form interlocking O-rings and pulling the thumb and the remaining finger of the patient apart whereby in electromagnetic field of the tissue of the sample interacts with an electromagnetic field of any identical cancerous tissue of the internal organ being probed and this interaction is detected by the ability to pull apart the O-ring shape.

15. A method of imaging an internal organ of a patient for purposes of medical diagnosis, comprising the steps of:

having the patient form an O-ring shape with one of his hands by placing the fingertips of his thumb and one of his remaining fingers of one of hands together;

placing a sample of a particular type of bacteria in the patient's other hand; and non-invasive external probing of an internal organ or the patient with probing means, and simultaneously attempting to pull apart the O-ring shape by means of a tester placing his thumb and one of his remaining fingers of each of his hands within the O-ring shape and pulling the thumb and the remaining finger of the patient apart whereby the an electromagnetic field of the bacteria sample interacts with an electromagnetic field of the internal organ affected by this particular bacteria being probed and this interaction is detected by the ability to pull apart the O-ring shape.

* * * * *